United States Patent [19]

Nivens et al.

[11] Patent Number: 5,922,536
[45] Date of Patent: Jul. 13, 1999

[54] METHOD FOR NUCLEIC ACID ISOLATION USING SUPERCRITICAL FLUIDS

[76] Inventors: David E. Nivens, 11912 Kingsgate Rd.; Bruce M. Applegate, 3700 Sutherland Ave. #Q2, both of Knoxville, Tenn. 37911

[21] Appl. No.: 08/733,816

[22] Filed: Oct. 18, 1996

[51] Int. Cl.⁶ ............................. C12Q 1/00; C12P 19/34; C07H 21/02; C07H 21/04
[52] U.S. Cl. ................................. 435/6; 435/4; 435/25.1; 435/91.2; 536/23.1; 536/25.41
[58] Field of Search .................................. 435/4, 6, 25.1, 435/91.2; 536/23.1, 25.41

[56] References Cited

U.S. PATENT DOCUMENTS

| | | | |
|---|---|---|---|
| 5,306,637 | 4/1994 | Lin et al. | 435/259 |
| 5,380,826 | 1/1995 | Castor et al. | 530/422 |
| 5,487,981 | 1/1996 | Nivens et al. | 435/30 |

FOREIGN PATENT DOCUMENTS 8702697  5/1987  WIPO ............................. C11B 1/10

OTHER PUBLICATIONS

Bej et al. Applied and Environmental Microbiology 57(12) : 3529–3534, 1991.
Yu–Li Tsai, Betty H. Olson, "Rapid Method for Direct Extraction of DNA from Soil and Sediments", *Applied and Environmental Microbiology*, Apr. 1991, pp. 1070–1074.
More, Herrick, Silva, Ghoirse, Madsen, "Quantitative Cell Lysis of Indigenous Microorganisms and Rapid Extraction of Microbial DNA from Sediment", *Applied and Environmental Microbiology*, May 1994, pp. 1572–1580.
Somerville, Knight, Straube, Colwell, "Simple, Rapid Method for Direct Isolation of Nucleic Acids from Aquatic Environments", *Applied and Environmental Microbiology*, May 1989, pp. 548–554.
Steffan, Goksoyr, Bej, Atlas, "Recovery of DNA from Soils and Sediments", *Applied and Environmental Microbiology*, Dec. 1988, pp.2908–2915.
Ogram, Sayler, Barkay, "The extraction and purification of microbial DNA from sediments", *Journal of Microbiological Methods 7*, 1987, pp. 57–66.
Picard, Ponsonnet, Paget, Nesme, Simonet, "Detection and Enumeration of Bacteria in Soil by Direct DNA Extraction and Polymerase Chain Reaction", *Applied and Environmental Microbiology*, Sep. 1992, pp. 2717–2722.
Nili Grossman, Eliora Ron, "Membrane–Bound DNA From *Escherichia coli*: Extraction By Freeze–Thaw–Lysozyme", *FEBS Letters*, Jul. 1975, vol. 54, No. 3, pp. 327–329.

Bej, DiCesare, Haff, Atlas, "Detection of *Escherichia coli* and Shigella spp. in Water by Using the Polymerase Chain Reaction and Gene Probes for uid", *Applied and Environmental Microbiology*, Apr. 1991, pp. 1013–1017.
Yu–Li Tsai, Betty Olson, "Rapid Method for Separation of Bacterial DNA from Humic Substances in Sediments for Polymerase Chain Reaction", *Applied and Environmental Microbiology*, Jul. 1992, pp. 2292–2295.
Yu–Li Tsai, Carol Palmer, Louis Sangermano, "Detection of *Escherichia coli* in Sewage and Sludge by Polymerase Chain Reaction", *Applied and Environmental Microbiology*, Feb. 1993, pp.353–357.
Holben, Jansson, Chelm, Tiedje, "DNA Probe Method for the Detection of Specific Microorganisms in the Soil Bacterial Community", *Applied and Environmental Microbiology*, Mar. 1988, pp. 703–711.
Johnson, Pieniazek, Griffin, Misener, Rose, "Development of a PCR Protocol for Sensitive Detection of Cryptosporidium Oocysts in Water Samples", *Applied and Environmental Microbiology*, Nov. 1995, pp. 3849–3855.
Bej, Mahbubani, Dicesare, Atlas, "Polymerase Chain Reaction–Gene Probe Detection of Microorganisms by Using Filter–Concentrated Samples", *Applied and Environmental Microbiology*, Dec. 1991, pp. 3529–3534.
Bej, Steffan, DiCesare, Haff, Atlas, "Detection of Coliform Bacteria in Water by Polymerase Chain Reaction and Gene Probes", *Applied and Environmental Microbiology*, Feb. 1990, pp. 307–314.
Rong–Fu Wang, Allison Luneau, Wei–Wen Cao, Carl Cerniglia, "PCR Detection of Polycyclic Aromatic Hydrocarbon–Degrading Mycobacteria", *Environ. Sci. Technol.*, 1996, pp. 307–311.
Gary Jones, Peter Nichols, Philip Shaw, "Analysis of Microbial Sterols and Hopanoids", *Chemical Methods in Prokaryotic Systematics*, pp.163–195.
"Preparation of Genomic DNA from Bacteria", *Basic Protocol*, Unit 2.4, 1987.
"Recovery of DNA from glass fiber filters after exposure to supercritical fluid conditions".

*Primary Examiner*—James C. Housel
*Assistant Examiner*—V. Ryan
*Attorney, Agent, or Firm*—Knobbe, Martens, Olson & Bear, LLP

[57] ABSTRACT

A method for detecting the presence of a microorganism in an environmental sample involves contacting the sample with a supercritical fluid to isolate nucleic acid from the microorganism, then detecting the presence of a particular sequence within the isolated nucleic acid. The nucleic acid may optionally be subjected to further purification.

11 Claims, 4 Drawing Sheets

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:1:

AGAGTTTGAT CMTGGCTCAG                                                    20

(2) INFORMATION FOR SEQ ID NO:2:

(i) SEQUENCE CHARACTERISTICS:
         (A) LENGTH: 17 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:2:

AAGGAGGTGW TCCARCC                                                       17

(2) INFORMATION FOR SEQ ID NO:3:

(i) SEQUENCE CHARACTERISTICS:
         (A) LENGTH: 15 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:3:

ACGGGCGGTG TGTRC                                                         15

(2) INFORMATION FOR SEQ ID NO:4:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:4:

AAGCTCGTAG TTGGATTTCT G                                                  21

(2) INFORMATION FOR SEQ ID NO:5:

(i) SEQUENCE CHARACTERISTICS:
         (A) LENGTH: 21 base pairs
         (B) TYPE: nucleic acid
         (C) STRANDEDNESS: single
         (D) TOPOLOGY: linear -continued (ii) MOLECULE TYPE: cDNA (xi) SEQUENCE DESCRIPTION: SEQ ID NO:5:

TAAGGTGCTG AAGGAGTAAG G 21

METHOD FOR NUCLEIC ACID ISOLATION USING SUPERCRITICAL FLUIDS

STATEMENT OF GOVERNMENT SUPPORT

A certain detail of the invention, relating to the use of supercritical $CO_2$ to isolate DNA from microorganisms in soil, was first tested using funds from the Department of Energy pursuant to Small Business Innovation Research (SBIR) Grant No. DE-FG02-95ER82027.

FIELD OF THE INVENTION

The present invention relates to an apparatus and method for the isolation of nucleic acids from microorganisms. More particularly, the invention relates to an apparatus and supercritical fluid method for the isolation of nucleic acids suitable for hybridization and/or amplification by the polymerase chain reaction.

BACKGROUND OF THE INVENTION

Since 1914, the safety of our water supply has generally been protected by the use of assays which detect the growth of certain types of bacteria, commonly referred to as indicator bacteria, to infer the presence of pathogens. Indicator bacteria, such as fecal coliforms and total coliforms, are found in fecal matter along with many pathogens. Although many indicator bacteria do not cause disease in humans, their presence indicates a potential risk of exposure to pathogens. As a result, water in which such bacteria are found will be declared unsafe for human contact therewith. Pathogens are not routinely assayed by direct methods due to difficulty in their isolation and detection. In contrast, indicator bacteria are cultured in 24 to 48 hours and can be detected visually. The main disadvantage with this detection method is that the results do not indicate the present water quality. In addition, indicator assays fail to accurately assess the infectivity of water. The risk is overestimated in environments which stimulate the growth of the non-pathogenic indicator microorganisms (i.e. warm, nutrient-rich waters). Conversely, certain waterborne pathogens (i.e. *Legionella* and *Naegleria fowleri*) are not transmitted through the feces and thus are not associated with fecal indicator organisms. Even in situations in which pathogens and indicator bacteria are from the same fecal source, the indicator bacteria may be killed more quickly than hardier pathogens such as protozoan cysts, viruses or bacterial spores. These and other problems could be eliminated by using assays which directly detect and quantitate waterborne pathogens.

More recently, the polymerase chain reaction (PCR), has been used in the detection and classification of various microorganisms. While DNA hybridization is useful in some applications, it carries the distinct disadvantage of having a high detection limit (low sensitivity). PCR, on the other hand, eliminates the need to culture the microorganism and is extremely sensitive—capable of detecting a single cell. The first and most critical step in both methods is, of course, the isolation of DNA of sufficient purity for analysis.

Several methods exist for the isolation of DNA from bacterial cells. These methods essentially utilize the same basic procedure. Bacterial cells are lysed enzymatically (i.e., lysozyme treatment), mechanically (i.e., bead homogenization) or by repeated freeze-thaw cycles, or combinations of these, followed by dissolution of the cell membrane with alkali and detergents such as sodium dodecyl sulfate (SDS) (Maniatis et al., 1989; Tsai et al., *Appl. Environ. Microbiol.*, 57:1070–1074, 1991; Bej et al., *Appl. Environ. Microbiol.*, 57:1013–1017, 1991). The cell lysate is then treated with proteinases and hexadecyltrimethyl ammonium bromide (CTAB) to degrade proteins and precipitate carbohydrates, respectively. The most common proteinase used in this procedure is proteinase K. Finally, DNA is purified by extraction with phenol, chloroform and isoamyl alcohol. Variations of this basic method have been used to isolate DNA from soils, sediments and water samples for use in hybridization and PCR analysis (Somerville et al., *Appl. Environ. Microbiol.*, 55, 548–554, 1989; Tsai et al., *Appl. Environ. Microbiol.*, 59:353–357, 1993; Bej et al., *Appl. Environ. Microbiol.*, 56:307–314, 1990). Although these methods can result in DNA of sufficient purity for both hybridization and PCR analysis, they are time consuming and involve expensive and toxic reagents. Further, the DNA obtained from soil and sediment samples is often of questionable purity and its analysis requires several days.

A substance in a supercritical fluid state is defined when it is above the critical temperature (the temperature above which the gas cannot be liquified no matter how high the pressure), and above the critical pressure (the pressure which will liquefy the gas at its critical temperature). At this point, the fluid has equal coexisting densities of its gaseous and liquid phases (*Lange's Handbook of Chemistry*, 13th ed, Dean, J. A., ed., McGraw-Hill, New York). The supercritical fluid is a viscous gas with properties analogous to those of liquid solvents (Hawthorne, *Anal. Chem.*, 62:633–642, 1990). The difference between liquid solvents and supercritical fluids is that the solvent strength of a supercritical fluid can be controlled by changes in temperature and/or pressure. The most commonly used supercritical fluid is carbon dioxide ($CO_2$) which is inert, nontoxic, nonflammable, inexpensive and available in a very pure form. $CO_2$ has a low critical temperature (31.1° C.) and critical pressure (72.85 atm).

Supercritical $CO_2$ has been used to extract a variety of nonpolar compounds from both biological and non-biological sources (Lin et al., *Biotechnol. Prog.*, 8:458–461, 1992). It has been used to extract alkanes, sulfur compounds, PCBs, pesticides and polycyclic aromatic hydrocarbons from soil and sediments (Hawthorne, ibid.; Hopfgartner et al., *Org. Geochem.*, 15:397–402, 1990), as well as fatty acid and sterol lipid biomarkers from plant tissue, sediments, and filtered water samples (Klink et al., *Org. Geochem.*, 21:437–441, 1994).

The number of viable microorganisms decreases after treatment with supercritical fluids. For example, cell inactivation of *Saccharomyces cerevisiae* increases with an increase in pressure at temperatures of 25–45° C. and pressures of 68–204 atm (Lin et al., ibid.). Under these conditions, inactivation occurred in greater than 15 minutes at 25° C. and 5 minutes at 35° C. Increases in pressure or exposure time were correlated with an increase in adverse effects, including microbial death (Hoover et al., *Food Technol.*, 43:99–107, 1989). When exposed to pressures of 300 to 450 atm, *Pseudomonas* exhibited morphological changes including cellular elongation, separation of the cell wall from the plasma membrane and clear areas of spongy or reticular structures in the cytoplasm (Hoover et al., ibid.; Kriss et al., *Mikrobiolgiya*, 38:88, 1969).

DNA appears very resistant to hydrostatic pressure. Structural integrity of calf thymus or salmon sperm DNA remained unchanged when pressures of up to 10,000 atm were applied for 60 min at 25–40° C.

The present invention provides an apparatus and method for the rapid isolation of DNA of high purity from microorganisms present in environmental samples including water, soil and sediments. Importantly, this method can be used to detect the presence of pathogenic microorganisms in water supplies.

SUMMARY OF THE INVENTION

One embodiment of the present invention is a method of identifying a microorganism in an environmental sample, comprising contacting the sample with a supercritical fluid to extract DNA therefrom; and detecting the presence of a nucleic acid sequence specific to the microorganism. Preferably, the microorganism is a bacterium. Alternatively, the microorganism is a protozoan, parasite or virus. Advantageously, the bacterium is *E. coli*. According to one aspect of this preferred embodiment, the sample is water, soil or sediment. Preferably, the supercritical fluid is supercritical $CO_2$. The method may further comprise applying the sample to a filter prior to the contacting step. In another aspect of this preferred embodiment, the detecting step is PCR or hybridization analysis. Preferably, the nucleic acid is DNA. Alternatively, the nucleic acid is RNA. The method may further comprise extracting the sample with one or more solvents or mixtures prior to the detecting step.

Another embodiment of the invention is a subassembly for extracting and purifying nucleic acid from microorganisms present in a sample, comprising:
 a sample cartridge comprising a filter for receiving said sample; and
 a collection cartridge comprising a matrix which binds nucleic acid fluidly connected to the sample cartridge.
Preferably, the filter is a bed filter. Advantageously, the subassembly is disposable. In one aspect of this preferred embodiment, the nucleic acid is DNA. Alternatively, the nucleic acid is RNA. Preferably, the sample is water, soil or sediment and the matrix is hydroxyapatite.

Another embodiment of the invention is an apparatus for isolating and extracting nucleic acid from microorganisms contained within an environmental sample, comprising:
 a sampling cartridge having an input end and an output end;
 a collection cartridge connected to the sampling cartridge at the output end, wherein the collection and sampling cartridges are surrounded by a high pressure compartment within a temperature- and pressure-controlled zone;
 a high pressure interface sealingly engaging the input end of the sample cartridge;
 a plurality of pumps fluidly connected to the sampling cartridge; and
 a controller electrically connected to one of the pumps.
Preferably, the nucleic acid is DNA. Alternatively, the nucleic acid is RNA. According to one aspect of this preferred embodiment, the pumps pump sample, supercritical fluid, organic solvents, or aqueous buffer. Advantageously, the sampling and collection cartridges are disposable. Preferably, the sampling and collection cartridges are made of plastic. In addition, the pressure- and temperature-controlled zone may comprise an aluminum block.

DETAILED DESCRIPTION OF THE PREFERRED EMBODIMENTS

Figure 1:
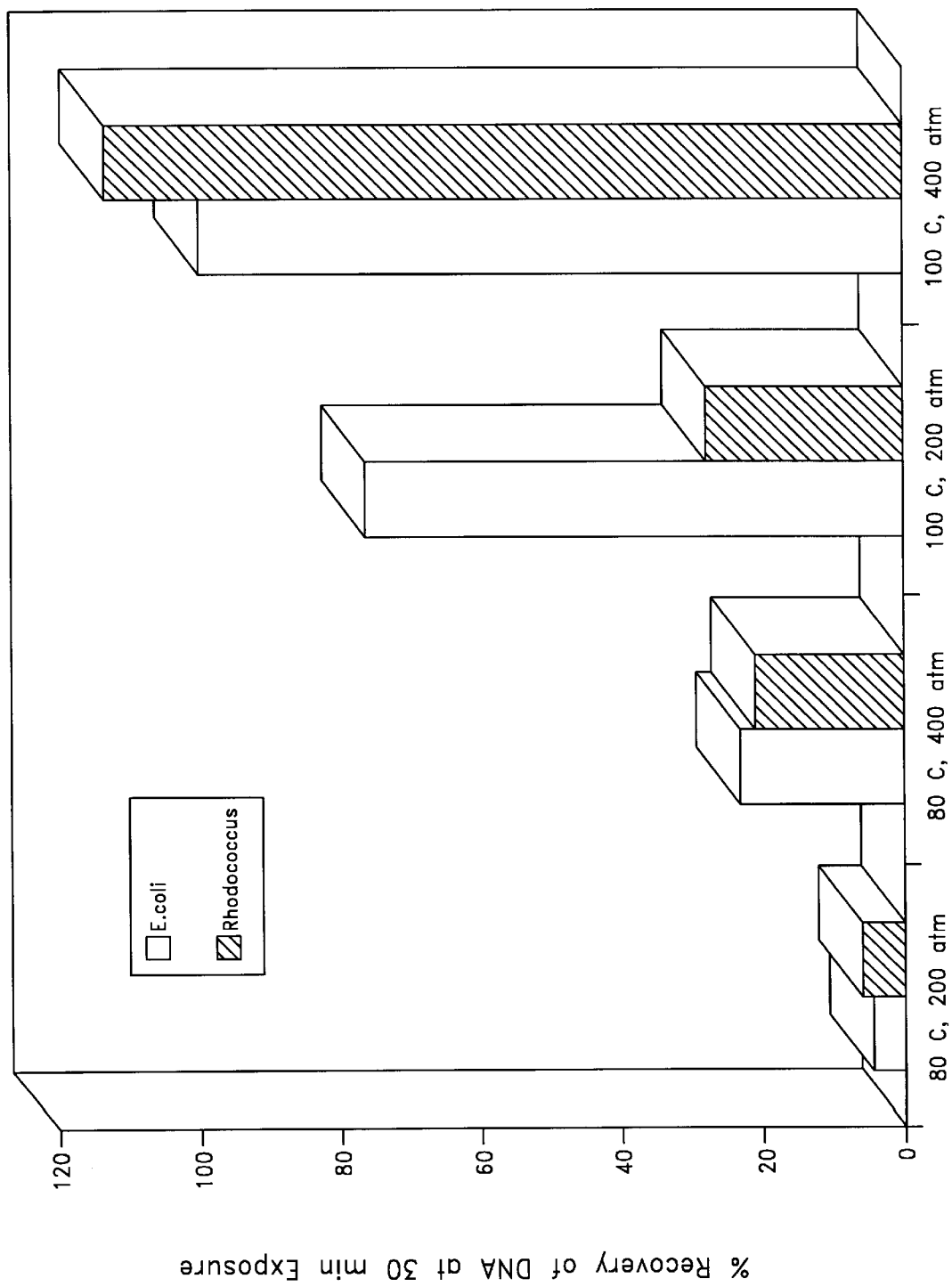
FIG. 1 is a bar graph showing the percentage of *E. coli* and Rhodococcus DNA recovered after supercritical $CO_2$ extraction under various conditions.

The present invention includes the observation that intact genomic DNA can be isolated by lysis of microbial cells with supercritical fluids. The method comprises exposure of microorganisms to supercritical fluids, resulting in cell lysis. Although the use of supercritical $CO_2$ is preferred, the use of other supercritical fluids including propane, sulfur hexafluoride, Freons, nitrous oxide and ammonia is also contemplated. Although the DNA obtained by this method can be used directly for hybridization analysis or PCR, it is preferably further purified by extraction with organic solvents (i.e., phenol, chloroform, isoamyl alcohol), polar solvents (i.e., ethanol, water), or combinations thereof. The DNA may also be treated with proteinases (i.e. proteinase K) to degrade proteins and with hexadecyltrimethyl ammonium bromide (CTAB) to precipitate carbohydrates.

The microorganisms which are detected are present in environmental samples, including water, sediments and soils. For detection of microorganisms in water samples, the water is passed through a filter and the microorganisms are retained on the filter. The microorganisms are lysed directly on the filter. Suitable filters include, for example, membranes, glass fiber filters and bed filtration devices. For soil and sediment samples, microorganisms may be separated from the sample prior to supercritical fluid isolation, or the microorganisms in the sample may be lysed directly, followed by removal of the nucleic acids from the soil or sediment. Extraction and purification of microbial DNA from sediments is discussed by Ogram et al. (*J. Microbiol. Meth.*, 7:57–66, 1987). The preferred method, direct lysis, may also comprise bead homogenization (More et al., *Appl. Environ. Microbiol,* 60:1572–1580, 1994). Pretreatment of the samples with organic solvents is also contemplated, as this procedure may facilitate cell wall degradation, thus increasing recovery.

A major advantage of the claimed nucleic acid isolation method is that it is universal for all microorganisms. A significant disadvantage of prior art lysis methods is that not all microorganism species are lysed by a particular procedure; in contrast, the instant method results in lysis of all species tested. This is important because if partial or preferential lysis occurs, the extracted DNA would not be representative of the population of microorganisms in the sample. The present method is rapid and results in the isolation of high-quality DNA. Another advantage of supercritical fluids, particularly $CO_2$, is that after lysis, the fluid is removed from the sample in the form of a gas reducing the risk of sample loss due to pipetting or some other transfer technique. Essentially, the lytic agent removes itself from the lysate rather than removing the lysate from the lytic agent. The supercritical properties of $CO_2$ thus eliminate the need for SDS as a lytic reagent. These current art procedures not only result in loss of sample, but in some cases are environmentally and physically unsafe.

Supercritical fluid may also be used to isolate RNA, including ribosomal RNA (rRNA) and messenger RNA (mRNA). Because of the ubiquitous presence of RNases, cell lysis and extraction must be performed in the presence of RNase inhibitors (i.e. RNasin) and all solutions should be made with diethyl pyrocarbonate (DEPC)-treated water. Additionally or alternatively, microbial or environmental samples are extracted with hot phenol/chloroform at 60° C. which reduces RNA degradation due to inactivation of endogenous and exogenous RNase. The RNA obtained by this method can be used for Northern hybridization analysis, reverse-transcription, in vitro translation and for constructing cDNA libraries. In contrast to DNA, RNA is not amplified directly, but is first transcribed into DNA by reverse transcriptase followed by amplification of the DNA. The detection of RNA is advantageous because multiple copies of the target RNA molecule may be present in the cell and some forms of RNA (i.e. mRNA) rapidly degrade after cell death. Rapid degradation of the target nucleic acid is important if definitive proof of viability or infectivity is to be demonstrated because DNA may persist for some time after cell death, resulting in detection of DNA from a nonviable pathogen.

DNA extracted from different environmental samples can be compared if they are normalized to the relative number of organisms originally present in the sample from which the total DNA was extracted. Typically, this normalization is performed by probing for the presence of 16S rRNA gene sequences in total DNA. A universal oligonucleotide probe complementary to the 16S rRNA gene of eubacteria is incubated with the extracted DNA blotted onto a nylon membrane (Stahl et al., *Appl. Environ. Microbiol.*, 54:1079–1084, 1988). The ratio between the frequency of a specific gene and the sequences hybridizing to the eubacterial probe in total DNA is then determined. In addition, if it is assumed that there are about 5 copies of 16S rRNA genes per eubacterial cell, the hybridization can be used to estimate the overall number of eubacteria in the sample.

An automated apparatus is used for extracting and purifying both RNA and DNA from microorganisms retained by filter systems such as filter beds or membrane filters. The nucleic acid extracts are suitable for analysis by both conventional and state-of-the-art detection techniques. Solutes, including phospholipids, steroids and pollutants in the supercritical fluid effluent and/or solvent extract can also be collected and analyzed by other conventional analytical techniques to provide complementary data to facilitate sample characterization. The apparatus prepares nucleic acids more rapidly and less expensively than standard methods allowing a more rapid detection of microorganisms contained in water samples, including waterborne pathogens such as *E. coli*, Shigella, Cryptosporidium and Giardia. The apparatus can be used to detect microorganisms present in recreational waters, source water and potable water.

In a preferred embodiment, the apparatus comprises a computerized controller, pumps, a nucleic acid isolation module and a preferably disposable subassembly containing a sample cartridge and a collection cartridge. The nucleic acid isolation device comprises a temperature- and pressure-controlled zone, manifolds with automated valves, high-pressure fluid seals to receive the subassembly and a computer interface board. In another preferred embodiment, the sample cartridge also serves as a filtration device. The disposable subassembly protects against cross-contamination. The first step, filtration, traps pathogens contained in the sample on a filter system such as a commercial disk filter (FIG. 2) or a filter bed housed in the sample cartridge (FIG. 3).

Disk filters have well-defined pore sizes (0.1 μm to 1 μm), good trapping efficiency and minimal dead volume which is important in minimizing the volume of solvent used for lysis, purification and sample collection. Filters of different pore sizes may be used in combination to maximize microorganism trapping efficiency. Filtration may be performed using the sampling cartridge as a filter holder or by using a user-supplied filtering apparatus.

Figure 2:
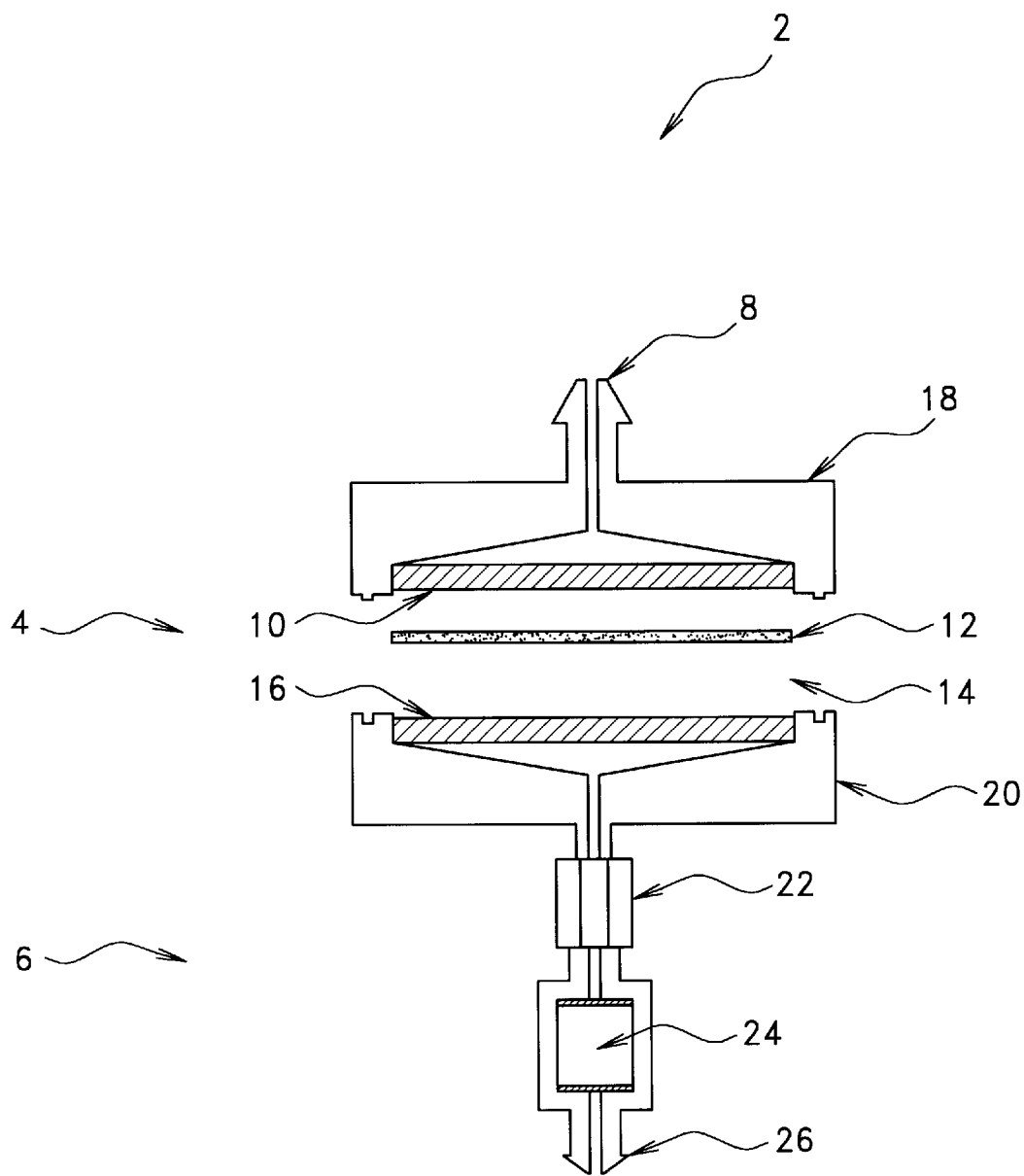
FIG. 2 is a schematic diagram showing the disk sampling cartridge and collection cartridge subassembly.
Figure 3:
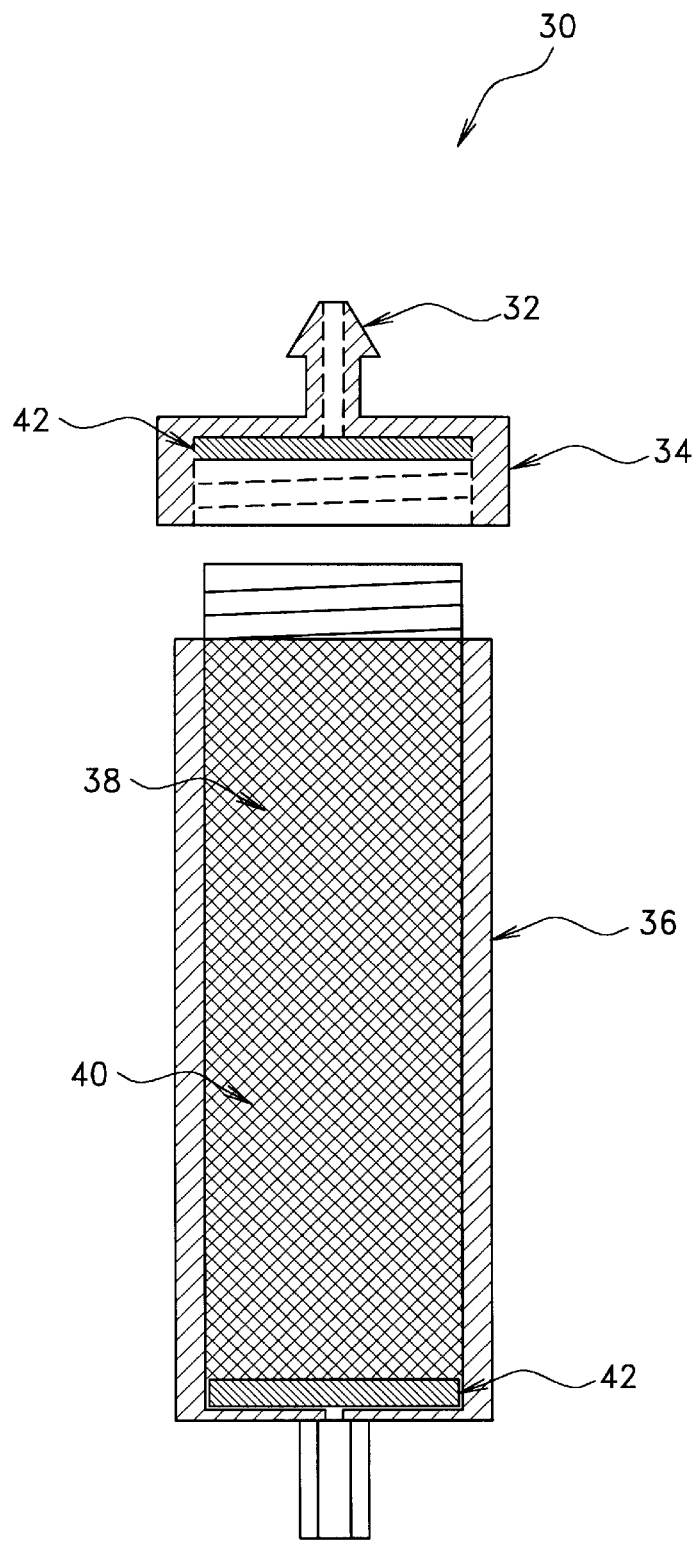
FIG. 3 is a schematic diagram of a bed filtration cartridge for use in the sampling cartridge and collection cartridge subassembly.
Figure 4:
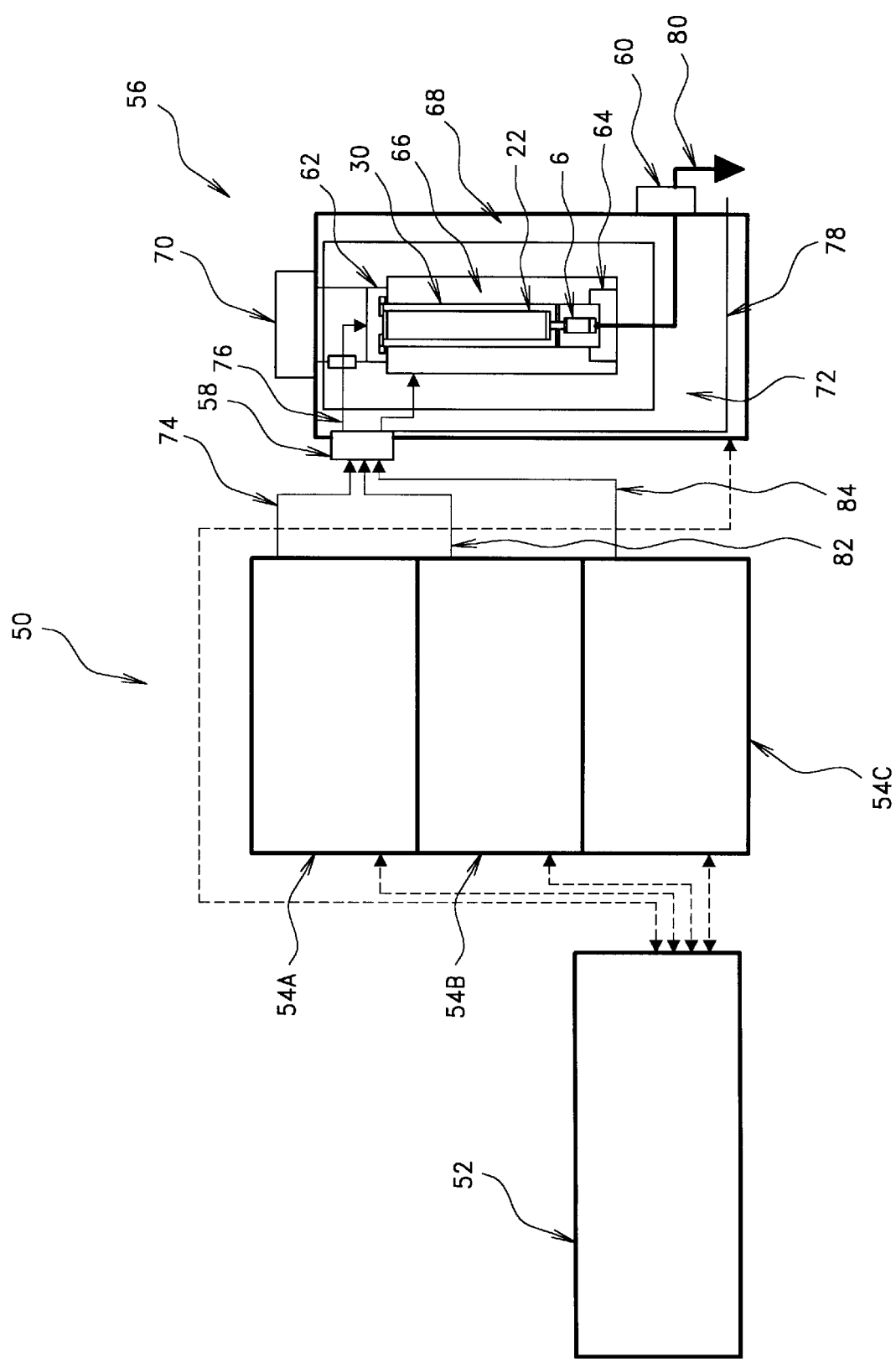
FIG. 4 is a schematic diagram of an integrated nucleic acid extraction and purification system.

FIG. 2 illustrates one embodiment of the subassembly 2 of the invention. The subassembly 2 contains a disk sampling cartridge 4 and a collection cartridge 6 for use in isolation of nucleic acids from environmental samples. When the sampling cartridge 4 is used as the filtering apparatus, the water sample passes through inlet 8, upper porous frit 10 and onto filter 12 within extraction chamber 14. Filtered samples pass through filter 12 and lower porous frit 16. Porous frits 10 and 16 are attached to upper module housing 18 and lower module housing 20, respectively. If a user-supplied filtering apparatus is used, the filter with trapped sample is placed in the sample cartridge and the cartridge sealed before nucleic acid isolation. The analysis of other samples including urine, sputum, blood plasma, activated sludge and fermentation broth, by this system is also contemplated. After filtration, the sampling cartridge 4 is fluidly sealed to collection cartridge 6 either by connector 22 or by an integral sealing system. The subassembly is then sealed within the temperature- and pressure-controlled zone of the nucleic acid isolation module (FIG. 4).

The subassembly 2 is pressurized with carbon dioxide and heated above the critical point (73 atm, 31° C.) to form a supercritical fluid. An exit valve is then opened to rapidly depressurize the system and rupture the microorganisms within the sample cartridge. Hot organic solvent, (i.e. phenol, ethanol, isopropanol) is then pumped through inlet 8 using standard commercially available pumps (FIG. 4) into the system to: 1) further degrade the cell matrix; 2) deactivate enzymes which degrade nucleic acids; and 3) remove contaminants.

Collection cartridge 6 is packed with a material 24 which has an affinity for nucleic acids. Such materials include hydroxyapatite, silica and ion-exchange resin. Aqueous buffer is then pumped through inlet 8 to transfer the nucleic acids from disk sampling cartridge 4 to collection cartridge 6. The trapped nucleic acids are removed from material 24 using appropriate buffers. For example, trapped nucleic acids are removed from the hydroxyapatite material 24 using 0.5 M sodium phosphate, pH 6.8. The eluted nucleic acids pass through outlet conduit 26 which is fluidly connected to cartridge 6, then analyzed by conventional techniques, including hybridization analysis, dot blot analysis and PCR. Detection kits containing the probes for specific pathogens may be prepared and used with the system. For example, probes can be selected for their ability to determine specific sources of fecal contamination in recreational waters. All reagents are provided in a kit, including filter cartridges, labeled oligonucleotides, PCR reagents and internal controls.

FIG. 3 shows an alternate sample cartridge configuration, the bed filtration cartridge 30 for use in the subassembly 2 shown in FIG. 2. Bed filtration cartridge 30 contains inlet 32 attached to cap 34. Cap 34 is threadedly sealed to cartridge housing 36 containing filter bed media 38 within extraction chamber 40. Porous frits 42 are situated inside chamber 40 above and below filter bed media 38. The bottom of chamber 40 is connected to the remainder of the subassembly by connector 22 as shown in FIG. 2. In this embodiment, the filter bed media 38 can be replaced with other particulate matter such as soil or sediment for analysis of the nucleic acids contained therein.

The complete automated nucleic acid purification and extraction system (NEPS) 50 is shown in FIG. 4. Parameters including pressure, temperature, composition of the supercritical fluid (modified or pure carbon dioxide) and solvent, exposure and extraction times and flow rates are set and monitored by controller 52 to optimize extraction efficiency. The system comprises a computerized controller 52, a plurality of pumps 54, and a nucleic acid isolation module 56. The nucleic acid isolation module 56 is equipped with inlet 58 and outlet 60 fluid manifolds, inlet seals 62, outlet seals 64, a temperature control block 66, a high pressure compartment 68 formed with the inlet sealing device 70 and the subassembly 2 containing the sampling 4 and collection 6 cartridges.

In a preferred embodiment, the temperature control block 66 is made of aluminum and heated by heating elements and, if needed, cooled with a Peltier device. In another preferred embodiment, the subassembly 2 is constructed of materials capable of withstanding high-pressure operation such as aluminum or steel, and sealed by the inlet sealing device 70 to the inlet manifold 58. In this embodiment, only the interior of the subassembly 2 is pressurized.

Samples are applied onto either filter beds or commercial disk filters housed within sample cartridge 4 which is preferably made of plastic. Alternatively, bed sampling cartridge 30 may be used in the NEPS. Application of samples is accomplished by vacuum filtration or use of head pressure to force aqueous solutions through the bed sampling 30 or disk 4 sampling cartridge. Optionally, aqueous solutions may be pretreated with flocculation or coagulation agents to increase filtration efficiency. Once a desired volume of liquid is filtered, the column is drained and detachable endcaps are affixed to minimize the risk of contamination. After filtration, the endcaps are removed from sample cartridge 30 and the nucleic acid collection cartridge 6 is connected to the sample cartridge 30 using connector 22. The nucleic acid collection cartridge is preferably made of plastic. The sample/collection cartridge subassembly is fluidly connected to an inlet sealing device 70 and sealed into the temperature- and pressure-controlled zone 72 of the NEPS. In a preferred embodiment, this step is performed automatically, directed by the controller 52. Alternatively, the connection and sealing may be done manually. Once sealed, the NEPS is pressurized with carbon dioxide via pump 54A which is fluidly connected to sample cartridge 30 through conduit 74, manifold 58 and conduit 76. The temperature control block 66 is sealed with a high-pressure interface to form the high pressure compartment 68 which contains the subassembly 2. To ensure that the pressure differential does not become great enough to damage the sample/collection cartridge subassembly 2, the pressure inside and outside the subassembly 2 is monitored during pressurization. External pressurization is accomplished by opening an automated valve within inlet manifold 58 which is in fluid communication with external pressurization conduit 78. Fluids are removed from the NEPS via outlet conduit 80.

The subassembly is also heated to a predetermined temperature before, after or simultaneously with pressurization. The protocol and setpoints for pressurization and heating can be determined using routine protocols well known to one of ordinary skill in the art to find those which maximize lysis efficiency for a pathogen of interest. Once pressurized and heated, the system is equilibrated and the sample is exposed to the supercritical fluid for a set period of time. Pump 54A pumps supercritical fluid through conduit 74, inlet manifold 58 and conduit 76 into sampling cartridge 30. After the temperature and pressure are raised above the critical point, then the liquid becomes supercritical. After a given period of time to allow supercritical fluid entry into the cells, typically several minutes, an exit valve is opened to rapidly depressurize the system. The process may be repeated to increase lysis efficiency. Supercritical fluid treatment is performed in either a static (no flow) or dynamic mode (i.e. flow rate of 1.5 ml/min). Dynamic treatment comprises opening an automated valve on the outlet manifold 60 to cause flow through a restrictor. At the end on the exposure time, the valve can be closed and the outlet valve opened for rapid depressurization. The controller 52 directs all valve openings and closings (manifold 58 and outlet conduit 80), as well as monitor and control temperature and pressure.

If required, hot organic solvent(s) is pumped with pump 54B through conduit 82, manifold 54 and conduit 76 into bed sampling cartridge 30 to further degrade the cell matrix; deactivate enzymes which can degrade nucleic acids; and remove contaminants. The temperature and pressure are again set and monitored by the controller. Carbon dioxide may be reintroduced into the system to remove any residual solvents. Aqueous buffer is pumped through sample cartridge 30 using pump 54C which is fluidly connected thereto via conduit 84, manifold 58 and conduit 76, to transfer the extracted nucleic acids to the collection cartridge 6. The subassembly 2 is removed from the NEPS and the collection cartridge 6 separated from the sampling cartridge 30. The trapped nucleic acids are eluted from the collection cartridge and amplified using conventional techniques, preferably PCR. In addition, the sample may be directly eluted into a PCR module to further avoid cross-contamination.

This apparatus bridges the gap between the environmental sample and modern molecular techniques such as PCR, thus providing direct evidence of the presence of pathogens within about 6 hours rather than days at a low cost. Solid phase collection columns may be used to collect, concentrate and purify the extracted DNA and RNA, thus preventing contamination thereof. Solid phases such as silica, hydroxyapatite, ion-exchange resin and other commercially available materials can be used.

In a preferred embodiment, due to the extremely high sensitivity of the PCR assay, the module for holding the filters during supercritical fluid isolation is disposable to eliminate cross contamination. Plastic extraction chambers can be used if both the inside and outside of the module are pressurized at the same time. Alternatively, plastic chambers may be inserted into high-pressure vessels to avoid damage to the chambers. The extraction chambers may be constructed of, for example, polyetheretherketone (PEEK), polyethylene, polypropylene and composite glass. The filter module may be of two general shapes: a cylindrical form packed with particular filter media, and a flat form using a membrane or filter as shown in FIG. 2. The flat form is particularly useful because it minimizes the dead space and the surface area of sample matrix. The modules may also be multi-use and constructed of metals such as stainless steel or aluminum.

Samples of various bacterial species were lysed using supercritical fluid as described in the following example.

Example 1

Sample Preparation and Supercritical Fluid Treatment

Cultures of *E. coli* were grown in LB broth (10 g Bacto-Tryptone, 5 g yeast extract, 10 g NaCl per liter) to 35° C. to an optical density (OD) of 1.0 at 546 nm. Cultures of

*Pseudomonas fluorescens* HK44 (King et al., *Science*, 249:778–781, 1990), *Sphingomonas paucimoblis* A8AN, *Mycobacterium* (Wang et al., *Environ. Sci. Technol.*, 30:307–311, 1996) and *Rhodococcus* sp. SM1 (Malachowsky et al., *Appl. Environ. Microbiol.*, 60:542–546, 1994) were grown in YEPG broth (1 g dextrose, 2 g polypeptone, 0.2 g yeast extract, 0.2 g $NH_4NO_3$ per liter) at 27° C. to an $OD_{546}$ of 1.0. Cells were collected by filtration of 1 ml culture through sterile 25 mm GF/F glass fiber filters (Whatman, Hillsboro, Oreg.). Bacterial concentration was determined by dilution plating and staining with acridine orange (Atlas et al., *Experimental Microbiology: fundamentals and applications*, second edition, MacMillan Publishing Co., New York, 1988).

SFE grade $CO_2$ was used as the supercritical fluid in an Isco SFX2–10 supercritical fluid extractor equipped with two 260D syringe pumps. The filters containing microorganisms were folded twice and clipped on the unfolded edge with a paper clip to avoid loss of cells. The samples were then placed in an extraction chamber and heated to the desired temperature. After 1 minute, the chamber was pressurized to the desired pressure. The restrictor valve was opened, and the fluid flowed through the extraction chamber at a rate of 1.5 ml/min. At the end of the run time, the outlet valve was opened and the inside pressure was rapidly reduced to atmospheric pressure. The filter was then removed for processing.

Example 2

Supercritical $CO_2$ Lysis Efficiency

Glass fiber filters containing cells lysed by supercritical $CO_2$ treatment were placed in microcentrifuge tubes to which a known volume of TE buffer had been added. The samples were vortexed for 20–30 seconds and a 10 μl aliquot was removed, applied to a 25 mm polycarbonate filter (0.2 μm pore size, Poretics, Livermore, Calif.) and stained with acridine orange. A serial dilution series was also prepared for inoculation on YEPG agar plates. The cell count determined by acridine orange staining after supercritical $CO_2$ treatment reflects the number of intact bacteria, while dilution plating represents the number of viable cells. The number of intact bacteria after treatment and the original bacterial concentration were used to calculate lysis efficiency. Lysis efficiency of *E. coli* was originally tested at different exposure times, pressures and temperatures and ranged from 74% to 97%. In general, favorable lysis was obtained at all conditions tested.

Similar experiments were performed at 80° C. and 400 atm using species of Pseudomonas, Sphingomonas, Mycobacterium and Rhodococcus. Results from lysis of these species under supercritical conditions were compared to those obtained using a conventional SDS lysis procedure (Table 1). For Pseudomonas, Sphingomonas and *E. coli*, the lytic action of supercritical fluids is comparable to that of SDS and, in the case of Rhodococcus and Mycobacterium, supercritical fluids are a better lytic agent. Dilution plate counts of lysed bacteria showed no growth after treatment with SDS or exposure to supercritical conditions, indicating that both methods result in loss of bacterial viability.

TABLE 1

|  | % SFF Lysis by AODC count | Standard Deviation | % SDS Lysis by AODC count | Standard Deviation |
| --- | --- | --- | --- | --- |
| *E. coli* | 88.83 | 2.98 | 90.23 | 1.85 |
| Pseudomonas | 90.31 | 6.88 | 94.09 | 8.39 |
| Sphingomonas | 68.61 | 22.39 | 99.32 | 0.65 |
| Rhodococcus | 74.11 | 8.28 | 2.85 | 50.5 |
| Mycobactenum | 78.88 | 6.87 | 59.03 | 19.78 |

Example 3

Recovery of DNA From Glass Fiber Filters

To determine a suitable buffer for recovery of DNA from glass fiber filters, $^{32}P$-labeled plasmid DNA was applied to the filters. The filters were placed in tubes containing either TE buffer (10 mM Tris-HCl, pH 8.0, 1 mM EDTA) or 0.12 M $Na_2HPO_4$.pH 8.0. The tubes were shaken for several minutes and an aliquot was placed in a scintillation vial to determine the amount of radio label released from the filters. TE buffer recovered 84.2±4.8% of the radio labeled DNA while $PO_4$ buffer recovered 57.3±1.5% of the DNA.

Example 4

Integrity of DNA After Exposure to Supercritical $CO_2$

To determine the integrity of DNA after exposure to supercritical conditions, the TA cloning vector pCRII having a length of 3.9 kb (Invitrogen, San Diego, Calif.) containing a 1.1 kb DNA insert was pipetted onto GF/F filters and exposed to supercritical conditions. The time of exposure varied from rapid pressurization-depressurization to 30 minutes in increments of 10 minutes. Experimental controls consisted of DNA which was placed on the filter, but was not exposed to supercritical conditions.

After exposure to supercritical conditions, the filters were placed in 1.5 ml Eppendorf tubes to which 750 μl TE buffer was added. The tubes were vortexed for 20–30 seconds. With the filter remaining in the tube, an equal volume of chloroform/isoamyl alcohol (24:1) was added to the tube and centrifuged for 5–6 minutes. This step was required due to breakdown of the glass fiber filters into particles which interfered with DNA recovery. This step allows removal of the glass particles which stay in the lower organic layer, while the DNA is in the upper aqueous layer. The aqueous layer, minus the filter, was removed and placed in a new tube. An equal volume of phenol/chloroform/isoamyl alcohol (25:24:1) was added and the samples were centrifuged for 5–6 minutes. The upper aqueous layer was recovered and precipitated with 0.1 volume 3 M sodium acetate and 2 volumes ice cold 100% ethanol. DNA was allowed to precipitate at –20° C. for >1 hour, then centrifuged for 20 min at 13,000 rpm. The DNA pellet was dried under vacuum and resuspended in 100 μl TE buffer (10 mM Tris-HCl, pH 8.0, 1 mM EDTA).

No detrimental effect was seen with DNA exposed to conditions of 80° C. or 100° C. and 400 atm for exposures of 20 minutes or less. Bands of intact plasmid DNA were observed in the control lane as well as the lanes containing plasmid DNA treated with supercritical fluid. Thus, the integrity of DNA is not compromised upon exposure to supercritical conditions.

Example 5

Recovery of DNA From Supercritical Fluid Treated Cells

DNA recovered from the five bacterial species was subjected to agarose gel electrophoresis and ethidium bromide staining. The stained gels showed bands of high molecular weight DNA with large quantities of low molecular weight nucleic acids present after exposure to supercritical conditions. RNase digestion of the samples followed by agarose gel electrophoresis revealed that the low molecular weight nucleic acid was exclusively RNA. Thus, the DNA recovered after exposure to supercritical fluid isolation was high molecular weight and had not been extensively degraded during the extraction process.

For comparison, DNA was also recovered from each bacterial species by traditional methods. For control purposes, genomic DNA was extracted from filtered and pelleted samples of each bacterial strain using the procedure of Ausubel et al. (*Current Protocols in Molecular Biology*, John Wiley & Sons, Inc., New York, 1987, hereby incorporated by reference). Filters were washed in 567 μl TE buffer. From this point on, the procedure was the same for both sets of controls. Cells were extracted with 30 μl 10% SDS, 3 μl Proteinase K (20 mg/ml) (Sigma, St. Louis, Mo.). The samples were incubated for 1 hour at 37° C., followed by addition of 100 μl 5 M NaCl and 80 μl CTAB. An equal volume of chloroform/isoamyl alcohol (24:1) was added to each sample followed by centrifugation for 5–6 minutes. The upper (aqueous) layer was removed and placed in a fresh tube, leaving the filter behind. The DNA was further purified by phenol-chloroform-isoamyl alcohol (24:24:1) extraction followed by precipitation with ethanol and sodium acetate as previously described.

Example 6

PCR Analysis After Supercritical Fluid Extraction

Universal primers which hybridize to 16s rRNA/DNA of most eubacteria were synthesized using a DNA synthesizer and purified using the Ultrafast cleavage and deprotection kit. Primers were resuspended in TE at a concentration of 1 μg/ml. The 27 f primer had the sequence 5'-AGAGTTTGATC(C/A)TGGCTCAG-3' (SEQ ID NO: 1) and the 1525r primer had the sequence 5'-AAGGAGGTG(A/T)TCCA(A/G)CC-3'(SEQ ID NO: 2). PCR conditions for amplification of the approximately 1.5 kb rDNA sequence were as follows: 5 minutes initial denaturation at 100° C.; 38 cycles at 94° C. for 1 minute (denaturation); 55° C. for 1 minute (cycling); 72° C. for 2 minutes (extension); then 72° C. for 10 minutes (final extension). Reactions were run in a total volume of 50 μl containing 0.05 U/μl Amplitaq DNA polymerase, 0.02 mM dNTPs, 10 μl PCR buffer (75 mM Tris-HCl, pH 9.5, 75 mM $(NH_4)_2SO_4$, 10 mM $MgCl_2$ for 5X), and 2 μl of each primer. Amplification of the 16s rRNA target sequence showed positive results with all five bacterial species without requiring further purification of DNA.

Example 7

DNA Hybridization After Supercritical Fluid Treatment

A universal 16s rRNA/DNA 15-mer oligonucleotide probe (5'-ACGGGCGGTGTGT(A/G)C-3') (SEQ ID NO: 3) was end-labeled with $^{32}P$ using T4 kinase. Sample DNA aliquots and 16s DNA standards were prepared in 0.4 M NaOH (final volume 0.5 ml) and boiled for 10 min. Samples and standards were blotted onto Biotrans™ nylon membrane (ICN, Irvine, Calif.) using a slot blot apparatus (Bio-Rad, Hercules, Calif.). Blots were rinsed and dried at 80° C. for 1 hour. The blot was prehybridized in 0.5 M sodium phosphate, pH 7.2, 1 mM EDTA, 7% SDS for 1 hour at 37° C. The $^{32}P$-labeled probe was added to the blot and incubated overnight. The blot was washed four times using a high stringency wash buffer (20 mM Tris-HCl, pH 7–8, 10 mM NaCl, 1 mM EDTA, 0.5% SDS, 37° C.). The blot was dried, exposed to x-ray film and hybridization signals were quantitated by densitometry using a Visage 110 digital imager (Millipore, Ann Arbor, Mich.). Integrated optical densities were calculated and hybridization signals were quantitated by interpolation from a calibration curve.

DNA hybridization analysis showed an increased recovery of DNA corresponding to increases in temperature and pressure. The conditions with the highest pressures and temperatures and longest exposure times (100° C., 400 atm, 30 min) produced the greatest yield of DNA compared to that obtained by standard SDS lysis procedures. Genomic DNA appears to be completely unaffected by the extremes of temperature and pressure used in supercritical fluid isolation.

Recovery of nucleic acids from Mycobacterium was 56% and increased to 61% when the samples were pretreated with $CHCl_3$. Nucleic acid recovery from Sphingomonas was 6% at 80° C., 400 atm for 30 minutes; however, $CHCl_3$ pretreatment increased the recovery to 45%, while chloroform:methanol (1:1) pretreatment resulted in recovery of 78% of the DNA compared to that of the SDS-treated bacterial cultures. The differing recoveries may be due to differences in cell membranes compared to the other bacterial species (i.e., the presence of mycolic acid in Mycobacterium and sphingoglycolipids in Sphingomonas).

Example 8

Recovery of DNA from Protozoa

Samples of *Cryptosporidium muris* oocysts were prepared by filtration onto GF/F glass fiber filters. Each filter contained approximately $2.63 \times 10^7$ oocysts. The filters were exposed to supercritical conditions of 400 atm at 100° C. for 30 minutes and the nucleic acids were recovered and analyzed by agarose gel electrophoresis and subsequent staining with ethidium bromide. Nucleic acids ranging from high to low molecular weight were visible. The nucleic acid extract was also subjected to PCR using primers specific to the *C. muris* 18s rRNA gene:

5'-AAGCTCGTAGTTGGATTTCTG-3' (SEQ ID NO: 4) (forward primer)

5'-TAAGGTGCTGAAGGAGTAAGG-3' (SEQ ID NO: 5) (reverse primer)

After an initial denaturation at 94° C. for 5 minutes, samples were reacted in a thermocycler for 38 cycles as follows: denaturation at 94° C. for 1 minute; annealing at 55° C. for 1 minute, and extension at 72° C. for 2 minutes. The final extension at 72° C. was performed for 10 minutes. Amplification of the expected 435 base pair target sequence (Johnson et al., *Appl. Environ. Microbiol.*, 61:3849–3855, 1995) was observed. These results demonstrate the successful lysis and recovery of nucleic acids from *C. muris* and detection of a specific DNA sequence using PCR.

It should be noted that the present invention is not limited to only those embodiments described in the Detailed Description. Any embodiment which retains the spirit of the present invention should be considered to be within its scope. However, the invention is only limited by the scope of the appended claims.

What is claimed is:

1. A method for identifying a species of microorganism in an environmental sample containing one or more species of microorganisms, comprising the steps of:

contacting said sample with a supercritical fluid to lyse said microorganisms and release nucleic acid therefrom;

extracting components other than nucleic acids from said lysate; and detecting the presence of a nucleic acid sequence specific to said species of microorganism by primer-mediated nucleic acid amplification, wherein the presence of said nucleic acid sequence indicates the presence of said species of microorganism.

2. The method of claim 1, wherein said microorganism is a bacterial species.

3. The method of claim 1, wherein said microorganism is a protozoan or parasite.

4. The method of claim 2, wherein said bacterial species is *E. coli*.

5. The method of claim 1, wherein said sample is selected from the group consisting of water, soils and sediments.

6. The method of claim 1, wherein said supercritical fluid is supercritical $CO_2$.

7. The method of claim 1, further comprising applying said sample to a filter prior to said contacting step.

8. The method of claim 1, wherein said detecting step is PCR or hybridization analysis.

9. The method of claim 1, wherein said nucleic acid is DNA.

10. The method of claim 1, wherein said nucleic acid is RNA.

11. The method of claim 7, wherein said components are extracted with one or more organic solvents.

* * * * *